United States Patent [19]

Anderson et al.

[11] 4,456,602

[45] Jun. 26, 1984

[54] AMINE CONTAINING ESTER PRODRUGS OF CORTICOSTEROIDS

[75] Inventors: Bradley D. Anderson, Kalamazoo; Robert A. Conradi, Portage, both of Mich.

[73] Assignee: The Upjohn Company, Kalamazoo, Mich.

[21] Appl. No.: 410,282

[22] Filed: Aug. 23, 1982

[51] Int. Cl.³ .......................... A61K 31/58; C07J 5/00
[52] U.S. Cl. .................................. 424/243; 260/397.45
[58] Field of Search .................. 260/239.5, 397.45; 424/243

[56] References Cited

U.S. PATENT DOCUMENTS

| | | | |
|---|---|---|---|
| 3,086,011 | 4/1963 | Hull | 260/239.5 |
| 3,883,569 | 5/1975 | Phillips et al. | 260/397.45 |
| 4,221,787 | 9/1980 | Bodor et al. | 260/239.5 |
| 4,242,334 | 12/1980 | Stache et al. | 424/243 |

FOREIGN PATENT DOCUMENTS

| | | | |
|---|---|---|---|
| 0737501 | 4/1969 | Belgium | 260/397.45 |
| 0831931 | 1/1976 | Belgium | 260/397.45 |
| 1102148 | 7/1959 | Fed. Rep. of Germany | 260/397.45 |
| 2459249 | 2/1981 | France | 260/397.45 |
| 0962797 | 7/1964 | United Kingdom | 260/397.45 |

*Primary Examiner*—Elbert L. Roberts
*Attorney, Agent, or Firm*—L. Ruth Hattan

[57] ABSTRACT

Novel solution stable ester prodrugs of corticosteroids of the formula

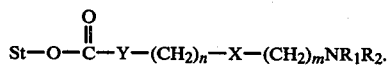

15 Claims, No Drawings

AMINE CONTAINING ESTER PRODRUGS OF CORTICOSTEROIDS

BACKGROUND OF THE INVENTION

Conventional anti-inflammatory steroids, such as cortisone, hydrocortisone, prednisone, methylprednisolone, etc., are generally poorly water soluble and therefore not suited for intravenous administration. Several types of soluble C-21 derivatives of such steroids have been disclosed in the patent literature including dicarboxylic acid hemiesters, sulfobenzoates, sulfopropionates, sulfates, phosphates, and aminoalkanoyloxy derivatives. While solubilization can generally be attained quite readily using a variety of such pro-moieties, most of the aforementioned derivatives possess other disadvantages limiting their utility as water soluble prodrugs. (The term "prodrug" denotes a derivative of an active drug which is converted after administration back to the active drug. The "pro-moiety" referred to in this application is the fragment attached to the steroid via an ester linkage and removed by ester hydrolysis in vivo.) A major problem with many common derivatives is their solution instability. Dicarboxylic acid hemiesters such as succinate esters, for example, are marketed commercially as lyophilized powders for reconstitution prior to injection due to their solution instability.

Numerous publications are available on the stability of 21-esters of corticosteroids. A partial listing of these articles and their content is given below:

*Factors Influencing Solvolysis of Corticosteroid 21-Phosphate Esters*, G. L. Flynn and D. J. Lamb, J. Pharm. Sci. 59, 1433 (1970).

*Stability of Corticosteroid Hemiesters of Dicarboxylic Acids*, E. R. Garrett, J. Pharm. Sci., 51, 445 (1962); E. R. Garrett, J. Med. Pharm. Chem., 5, 112 (1962); B. D. Anderson and V. Taphouse, J. Pharm. Sci., 70, 181 (1981); R. Yamamoto, S. Fujisawa, and M. Kawamura, Yakugaku Zasshi, 91, 855 (1971).

*Stability of Corticosteroid 21-Aminoalkylcarboxylates*, M. Kawamura, R. Yamamoto, and S. Fujisawa, Yakugaku Zasshi, 91, 863 (1971).

*Stability of Corticosteroid 21-Sulfobenzoates and 21-Sulfate*, M. Kawamura, R. Yamamoto, and S. Fujisawa, Yakugaku Zasshi, 91, 871 (1971).

Certain derivatives which do appear to exhibit sufficient solution stability may not be readily converted to the active drug in vivo. The 21-sulfate ester of hydrocortisone, for example, exhibits good solution stability but is inactive in mice. Other derivatives may possess the requisite solubility, stability, and bioconversion, but exhibit other disadvantages. Several undesirable features of phosphate esters, for example, are apparent: (1) Phosphate esters are often difficult to purify and are frequently very hygroscopic. (2) The stability of phosphate esters is optimum above pH 7 where other modes of drug degradation may be a problem. Glass surfaces are also more likely to delaminate in alkaline conditions resulting in particulate problems. (3) Precipitation of free corticosteroid due to the limited amount of hydrolysis which does occur may limit product shelf-life. Solubilization of free corticosteroid by the intact prodrug is a desirable feature which phosphate esters exhibit to only a limited extent.

The present invention provides a class of compounds which overcome these problems, providing novel solution stable prodrugs of corticosteroids.

FIELD OF INVENTION

The present invenytion is novel amine containing ester prodrugs of corticosteroids and formulations of steroid prodrugs.

SUMMARY OF INVENTION

The compounds of the present invention are amine containing ester prodrugs of corticosteroids which are solution stable in vitro but are rapidly converted in vivo to the active parent drug and are therefore useful as anti-inflammatory agents. The compounds of the present invention are represented by the following general Formula I

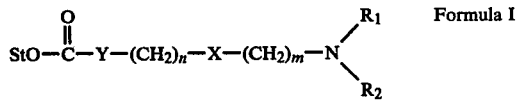

Formula I wherein St represents a corticosteroid moiety bonded to the carbonyl via the 21-hydroxyl group of said corticosteroid; Y is a bond, —O—, or —S—; X is

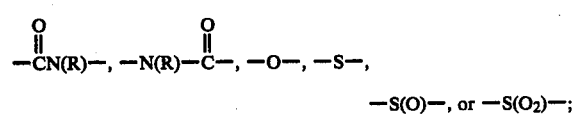

$$-S(O)-, \text{ or } -S(O_2)-;$$

n is an integer of from 2 to 9;
m is an integer of from 1 to 5; with the proviso that the sum of m and n is not greater than 10;
R is H or lower alkyl of from 1 to 4 carbon atoms;
$R_1$ and $R_2$ are the same or different and represent a lower alkyl of from 1 to 4 carbon atoms which is optionally substituted by one hydroxyl group, or —$NR_1R_2$ taken together form a monocyclic heterocyclic group selected from pyrrolidino, piperidino, morpholino, thiomorpholino, piperazino and N-(lower)alkyl piperazino, preferably N-methylpiperazino; with the proviso that when n is 2 or 3 and X is

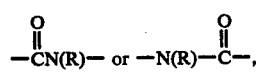

R is lower alkyl.

Pharmaceutically acceptable acid addition salts and quaternary ammonium derivatives of the compounds of Formula I are also a part of the present invention. Solution stable formulations of the compounds of Formula I are also a part of the present invention.

The present invention also includes solution stable formulations of compounds of the following Formula II

Formula II wherein St has the meaning defined in Formula I; $R_{30}$ is —$(CH_2)_p$—$Z_1$—$(CH_2)_p$— or —$Z_2$—$(CH_2)_p$— wherein p is an integer of from 1 to 8, $Z_1$ is —O— or —S—, and $Z_2$ is a bond, —O—, or —S—; and $R_{31}$ is piperazino or N-(lower)alkylpiperazino, preferably N-methylpiperazino; and pharmaceutically acceptable acid addition salts and quaternary derivatives thereof.

Any reference herein to the compounds of Formulas I or II is intended to include pharmaceutically acceptable salts and quaternary derivatives thereof.

DETAILED DESCRIPTION OF INVENTION

In the compounds of general Formulas I and II St represents the parent corticosteroid minus the 21-hydroxyl group of said corticosteroid which is necessary to form the novel esters of the present invention. The parent corticosteroid could be depicted as StOH wherein the OH is located at the 21-position of the corticosteroid which may be depicted as follows:

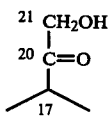

Of course the carbon atoms at positions C-17 and C-21 may be substituted as will be apparent from the description hereinbelow.

The term corticosteroid as used herein is taken to mean not only the steroids produced by the adrenal cortex but also synthetic equivalents, i.e., non-naturally occurring steroids which possess physiological properties characteristic of naturally occurring corticosteroids. Reference is made to Drill's Pharmacology in Medicine, McGraw-Hill Book Company, New York, (1965), Chapter 73: Adrenal Cortex and Adrenocortical Hormones, particularly pages 1185–1187 wherein typical corticosteroids employed in the present invention are described. Also, typical corticosteroids represented by StOH include those described in Applezweig, Steroid Drugs, McGraw-Hill Book Company, Inc., New York, 1962, pp. 435–731, and in particular the compounds associated with the following parenthetical numbers: 675; 684; 685; 734; 1030, 1033; 1034; 1035; 1036; 1038; 1039; 1048; 1051; 1052; 1059; 1061; 1063; 1064; 1066; 1067; 1068; 1070; 1071; 1072; 1073; 1078; 1080; 1082; 1083; 1084; 1086; 1087; 1088; 1092; 1093; 1094; 1095; 1099; 1100; 1101; 1105; 1107; 1108; 1109; 1110; 1111; 1112; 1116; 1116-A; 1117; 1119; 1120; 1121; 1125; 1128; 1135; 1140; 1141; 1142; 1143; 1149; 1151; 1155; 1168; 1169; 1170; 1172; 1173; 1174; 1175; 1176; 1178; 1181; 1182; 1182-A; 1183; 1184; 1186; 1187; 1189; 1193; 1194; 1197; 1198; 1206; 1207; 1214; 1215; 1216; 1217; 1218; 1220; 1221; 1226; 1227; 1230; 1231; 1242; 1243; 1244; 1246; 1248; 1251; 1270; 1272; 1273; 1274; 1275; 1279; 1280; 1281; 1282; 1283; 1285; 1286; 1287; 1294; 1295; 1296; 1306; 1307; 1308; 1319; 1320; 1322; 1323; 1324; 1325; 1327; 1328; 1329; 1330; 1331; 1333; 1334; 1336; 1337; 1338; 1339; 1340; 1350; 1351; 1352; 1363; 1368; 1370; 1385.

Also, typical corticosteroids represented by StOH include those described in Applezweig, Steroid Drugs, Holden-Day, Inc., San Francisco, 1964, pp. 109–438, and in particular the compounds associated with the following "catalogue" numbers:

2680; 2681; 2709; 2713; 2714; 2716; 2717; 2719; 2720; 2722; 2723; 2724; 2725; 2726; 2727; 2728; 2729; 2730; 2731; 2732; 2733; 2734; 2735; 2736; 2737; 2738; 2739; 2740; 2741; 2742; 2743; 2744; 2745; 2746; 2814; 2826; 2827; 3036-A; 3036-B; 3036-C; 3036-D; 3036-E; 3036-F; 3036-G; 3036-H; 3036-I; 3036-J; 3036-K; 3036-L; 3036-M; 3036-N; 3036-O; 3036-P; 3036-Q; 3036-R; 3036-S; 3036-T; 3036-U; 3036-V; 3052; 3054; 3057; 3071; 3073; 3074; 3075; 3078; 3081; 3082; 3087; 3088; 3090; 3108; 3109; 3109-A; 3111; 3112; 3112-A; 3114; 3117; 3118; 3119; 3119-A; 3120; 3121; 3122; 3122-A; 3123; 3124; 3130; 3131; 3132; 3133; 3139; 3140; 3141; 3142; 3143; 3143-A; 3145; 3147; 3148; 3151; 3152; 3154; 3168; 3169; 3170; 3171; 3171-A; 3174; 3175; 3175-A; 3178; 3180; 3181; 3182; 3183; 3184; 3184-A; 3189; 3191; 3192; 3193; 3193-A; 3196; 3198; 3199; 3200; 3201; 3202; 3203; 3204; 3205; 3206; 3215; 3216; 3217; 3218; 3220; 3222; 3226; 3227; 3231; 3232; 3232-A; 3234; 3235; 3235-A; 3237; 3238; 3239; 3240; 3241; 3242; 3242-A; 3248; 3249; 3250; 3251; 3251-A; 3253; 3254; 3255; 3256; 3257; 3258; 3259; 3260; 3265; 3266; 3267; 3268; 3269; 3273; 3287; 3288; 3289; 3289-A; 3291; 3292; 3293; 3293-A; 3296; 3297; 3298; 3299; 3300; 3301; 3302; 3303; 3303-A; 3316; 3317; 3318; 3319, 3319-A; 3332; 3333; 3334; 3335; 3337, 3338, 3339; 3340; 3341; 3342; 3343; 3344; 3345; 3346; 3347; 3349; 3350; 3351; 3372; 3373; 3373-B; 3374; 3375; 3376; 3377; 3379.

The corticosteroid field, i.e., the compounds and their use as pharmacologically active agents is well documented, and numerous other references exist which describe the synthesis and use of croticosteroids as depicted above by StOH. Substantially any corticosteroid having a hydroxyl group at the C-21 position of the molecule is useful as the parent steroid in forming the novel esters of the present invention. The compounds of Formulas A and B represent preferred corticosteroids used to contribute the St moiety of the compounds of Formulas I and II. Particularly preferred corticosteroids which are useful in forming the esters of Formulas I and II are the following: hydrocortisone, cortisone, corticosterone, prednisone, prednisolone, 6α-methyl-prednisolone, triamcinolone, dexamethasone, betamethasone, flumethasone, 11-deoxy corticosterone, fluprednisolone, 9α-fluorohydrocostisone, flurandrenolone, paramethasone, chloroprednisone, and dehydrocorticosterone. The compounds of Formula I wherein n is 4 to 9, and particularly 4 to 6, are more preferred. Also the compounds of Formula I wherein Y is a bond or X is

are more preferred.

Lower alkyl of from 1 to 4 carbon atoms includes methyl, ethyl, n-propyl, n-butyl, and isopropyl, and when optionally substituted by one hydroxyl illustrative of such groups are 2-hydroxyethyl, 2-hydroxypropyl and 3-hydroxypropyl.

Illustrative examples of pharmaceutically acceptable acid addition salts of the compounds of Formulas I and II are inorganic salts such as hydrochloride, hydrobromide, sulfate, phosphate; or organic salts such as acetate, malonate, succinate, or sulfonates or others as formed by treatment with a suitable acid as set forth hereinbelow.

The quaternary ammonium derivatives of the compounds of the present invention may be represented by Formula I wherein the terminal amine group is substituted by an additional group as depicted below:

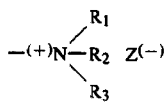

wherein $R_1$ and $R_2$ alone or taken together with the nitrogen atom to which each is attached have the meanings defined hereinabove; $R_3$ is a lower alkyl group of from 1 to 4 carbon atoms, preferably methyl or ethyl; and $Z^{(-)}$ represents an anion for example Z is I, Br, Cl, $CH_3SO_3$, or $CH_3COO$. The quaternary ammonium derivatives of the compounds of Formula II wherein $R_{31}$ is N-(lower)alkylpiperazinyl are further substituted at the 4-position of the piperazinyl ring with an $R_3$ group defined above forming a cation which is counterbalanced with an anion as defined by Z.

The compounds of Formulas I and II are prodrugs of the corticosteroids represented by the St moiety in said Formulas and have the same utility as the known or parent corticosteroid. Thus the compounds of Formulas I and II are useful in treating warm blooded animals, e.g., dogs, cats, monkeys, horses, and particularly humans for various disease conditions. For example, the compounds of Formulas I and II are useful in those situations where one wishes to elicit an anti-inflammatory, anti-pruritic or vasoconstrictive action inherent in the parent corticosteroid. The compounds of the present invention and the compounds utilized in the novel formulations of the present invention are particularly useful in treating acute adrenal insufficiency (Addison's disease); allergic conditions such as asthma, contact dermatitis, serum sickness, angioneurotic edema, drug hypersensitivity reactions and anaphylactoid reactions; collagen and musculoskeletal diseases, such as, rheumatoid arthritis, dermatomyositis, lupus erythematosus, rheumatic fever; dermatological diseases, such as, pemphigus and severe erythema multiforme; ulcerative colitis, and acute exacerbations of multiple sclerosis. Also when the parent corticostoid contributing the St moiety of the compounds of Formulas I and II possesses mineralocorticoid properties said compounds of Formulas I and II are useful particularly in maintaining a physiological electrolyte level in patients with acute adrenal insufficiency.

Although the compounds of Formula I, salts and quaternary derivatives thereof may be administered orally, these compounds are designed for and have their primary application in those situations where oral therapy is not feasible. The compounds of Formula I and the solution stable formulations of the compounds of Formula II are best suited for administration as sterile aqueous solutions by intravenous injection, intravenous infusion, or intramuscular or subcutaneous injection, or intravenous bolus.

The novel compounds of the present invention provide marked advantages over known corticosteroids of derivatives thereof in that these novel compounds are highly water soluble and when formulated in a manner which fully exploits the advantageous physicochemical properties of these compounds are sufficiently stable in aqueous solution to afford long term storage of solutions of said novel compounds.

The solution stability of these compounds is due to several features: (1) The derivatives are highly soluble in the pH range 3.5-4.5 which is the pH range in which ester hydrolysis in aqueous solution is minimized. (2) The amino-group, which in its protonated state can strongly activate esters toward hydroxide ion catalyzed hydrolysis, is sufficiently distant from the ester linkage that its undesirable substituent effect is minimal. (3) The compounds self-associate in concentrated solutions to form molecular aggregates which increase the shelf life of formulations by (a) retarding ester hydrolysis at high concentrations, and (b) solubilizing any parent corticosteroid present in and resulting from the hydrolysis of a solution of a compound of the present invention.

Examples of the attainable shelf life of compounds of Formulas I and II are presented in Table I. These estimates were obtained from the ratio of the solubility of the parent corticosteroid in formulations of the prodrug over the initial rate of formation of the parent corticosteroid in formulations stored at 30° C. The formulations were prepared by dissolving the required amount of compound in buffer and diluting to give a 0.2 M solution of the ester. The solutions were prepared in very dilute buffers (acetate, 0.1 $\mu$M) and the solution pH was adjusted to 4.25-4.5 by using either aqueous sodium hydroxide or hydrochloric acid.

TABLE I

| Example | Estimated Shelf Life (Years) |
|---------|------------------------------|
| 2 | 2.3 |
| 3 | 2.8 |
| 6 | 1.0 |
| 7 | 1.5 |
| 14 | 1.4 |

Obviously each of the compounds of Formulas I and II will differ to some extent in the lability of its ester linkage due to variations in the electronic and steric environment contributed by the pro-moiety. In addition, factors such as pH, solution concentration, and storage temperature have a dramatic impact on the stability of formulations. However, in formulations buffered at a pH at or near the pH-hydrolysis rate minimum (3.5-4.5) and at temperatures of 25°-30° C. regardless of concentration, the compounds of the present invention are solution stable for several months, and as indicated by the data provided above, some of the compounds in concentrated solutions are stable for up to two or more years at these temperatures. The stability or shelf life of solutions of compounds of the present invention can be prolonged by decreasing the storage temperature, e.g., to temperatures from 4° to 24° C.

As indicated previously, the compounds of Formulas I and II exhibit stability in water only when the pH of their solution is properly controlled. Ideally, the pH will be maintained at a level where the hydrolysis of the ester is at a minimum. This minimum depends to a certain degree on the chemical structure of the pro-moiety, the formulation concentration, and the temperature of storage but in general will be at a pH of about 3.5 to 4.5 for the compounds of this invention. Most advantageously, buffers should be employed to maintain the pH at or near the desired level throughout the shelf life of the formulation. Suitable buffers are those which are physiologically acceptable and exhibit sufficient buffer capacity in the pH range 3.5-4.5, e.g., acetate, citrate, succinate, or phthalate buffers and the like. The quantity of buffer used is determined by means known in the art and will depend on the pH desired, the concentration of the solution, and the buffering capacity of the buffer.

The concentration of the solution stable formulations of the compounds of Formulas I and II depends on the activity level of and the ultimate dose of parent corticosteroid desired. In general the stability of the formulations increases as the concentration of novel ester increases. In essence the solution stable formulations may be as concentrated as viscosity properties permit or until the solubility of the novel ester is exceeded. Inasmuch as the compounds of the present invention are converted to the parent corticosteroid in vivo, ideally the concentration of the novel ester and the volume of the solution administered will be chosen to provide a quantity of parent corticosteroid which is known to be effective. For example, a 0.267 M solution of the compound in Example 3, set forth below, is equivalent to 100 mg/ml of 6α-methylprednisolone.

Sterile aqueous solutions of the compounds of Formulas I and II typically will contain other components such as preservatives, antioxidants, chelating agents, or other stabilizers. Suitable preservatives can include benzyl alcohol, the parabens, benzalkonium chloride, or benzoic acid. Anti-oxidants such as sodium bisulfite, ascorbic acid, propyl3,4,5-trihydroxy benzoate, and the like may be employed. Chelating agents such as citrate, tartrate, or ethylenediaminetetraacetic acid (EDTA) may be used. Other additives useful as stabilizers of corticosteroid prodrugs (e.g., creatinine, polysorbate 80, and the like) may be employed.

Typical formulations useful in practicing the present invention are set forth below.

To demonstrate the bioconversion of the compounds of Formulas I and II to the parent steroid in serum, samples of human serum from males and from females were spiked with approximately 1 mg/ml of a compound of Formula I and warmed to 37° C. in a water bath. Aliquots of 200 μl each were withdrawn at timed intervals and quenched with 10 ml of 18% methanol, 1.2% acetic acid and water and analyzed using HPLC. Half-lives of the novel esters for conversion to the parent steroid were calculated from a plot of parent steroid concentration against time. The average of the half-lives in hours for the compounds of Examples 1, 2, 3 and 14 set forth below as determined in the male and female serum samples are 0.33, 0.20, 0.30 and 1.13 hours, respectively.

To demonstrate the bioconversion of the compounds of Formulas I and II to the parent steroid in vivo the following experiment was performed. Four female monkeys having synchronized menstrual cycles were given an separate days at least three days apart doses of the compound of Example 3 equivalent to 1.5 mg/kg and 7.5 mg/kg. Prior to dosing the monkeys were fasted overnight and each was anesthetized during dosing. The test compound was dissolved in 1 ml of 0.9% sodium chloride just prior to injection. Blood samples were withdrawn at times 0, ¼, ½, 1, 2, 4 and 8 hours from administration of test compound and levels of test compound and parent steroid were measured. In each monkey at either dose the test compound was completely converted to parent steroid, i.e., 6α-methylprednisolone, within one hour.

The compounds of Formulas I and II may be prepared by various means, and it will be apparent from the following that the ester moiety attached at the 21-position of the steroid, St, may be introduced by reaction of the steroid with an appropriate starting material amine which provides the entire moiety, or said ester moiety may be introduced by a sequence of one or more reactions.

The compounds of Formula II wherein $R_{30}$ is $-Z_2-(CH_2)_p-$ and $Z_2$ is a bond are prepared as described in U.S. Pat. No. 4,221,787.

In preparing the compounds of Formula I wherein Y is oxy, i.e., —O—, equimolar amounts of an amine of the formula

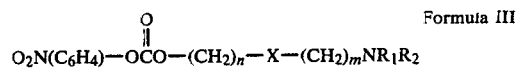
Formula III wherein ($C_6H_4$) is 1,4-phenylene and n, m, X, $R_1$ and $R_2$ have the meanings defined in Formula I, and a parent steroid of the formula StOH wherein St has the meaning defined in Formula I are reacted in a dry aprotic solvent such as tetrahydrofuran (THF), dimethylformamide (DMF) or dimethylsulfoxide (DMSO), in the presence of an acylation catalyst such as dimethylaminopyridine (DMAP) or N-methylimidazole. Although the reaction may be performed at room temperature it is convenient to gently warm the reaction mixture to about 50°-60° C. with stirring until all the activated carbonate ester is consumed. The product is isolated by pouring the reaction mixture into water with the pH adjusted to 2-4, washing with an organic solvent, e.g., ether or ethyl acetate, then quickly adjusting the pH to 7-8 and extracting with an organic solvent such as ethyl acetate. The product is isolated by removing the solvent and purified by recrystallization or chromatographic techniques.

The compounds of Formula II wherein $Z_2$ is oxy, i.e., —O—, are prepared in a manner similar to that described hereinabove only using a compound of the following Formula IIIA in place of a Formula III compound

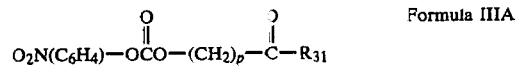
Formula IIIA wherein ($C_6H_4$) is 1,4-phenylene and p and $R_{31}$ have the meanings defined in Formula II.

To prepare compounds of Formula I wherein Y is sulfur, i.e., —S—, equimolar quantities of an appropriate thiol amine of the formula

Formula IV wherein n, m, x, $R_1$ and $R_2$ have the meanings defined in Formula I, and a chloroformate derivative of the parent steroid represented by the formula

Formula V wherein St has the meaning defined in Formula I with an equivalent quantity of a tertiary amine, such as triethylamine, are reacted in a dry aprotic solvent such as, THF, DMF or DMSO. The reaction mixture may be warmed gently if desired. The product is isolated by extraction with an organic solvent such as ethyl acetate or hexane and purified by crystallization or chromatography.

The compounds of Formula II wherein $Z_2$ is sulfur, i.e., —S—, are prepared in a manner similar to that described hereinabove only using a compound of the following Formula IVA in place of a Formula IV compound

Formula IVA wherein p and $R_{31}$ have the meanings defined in Formula II.

The compounds of Formula I wherein Y is a bond are prepared by reacting equimolar amounts of an amino acid of the formula $$HOC(CH_2)_n-X-(CH_2)_m-NR_1R_2 \quad \text{Formula VI}$$
(with C=O)

wherein n, m, X, $R_1$ and $R_2$ have the meanings defined in Formula I with a 21-iodo or 21-O-mesyl derivative of the parent steroid which may be represented respectively by the formulas $$St-Iodo \quad \text{Formula VII}$$

and $$St-O-mesyl \quad \text{Formula VIII}$$

wherein St has the meaning defined in Formula I and mesyl means $-S(O_2)-CH_3$. When the 21-iodo steroid derivative is employed the reaction proceeds at room temperature, whereas when the 21-O-mesyl steroid derivative is used the reaction is heated. Preferably both reactions are heated to about 60°–70° C. The reaction is carried out in a dry aprotic solvent such as DMF in the presence of a sterically hindered tertiary amine such as diisopropylethylamine. The product is isolated by extraction with an organic solvent, suitably ethyl acetate, and purified by recrystallization or chromatography.

Compounds of Formula I wherein Y is a bond and X is $$-\overset{O}{\underset{\|}{C}}N(R)-$$

may also be prepared by reacting equimolar amounts of a 21-iodo steroid derivative of Formula VI and a bis-acid of the formula $$HOC-(CH_2)_n-COH \quad \text{Formula IX}$$
(with two C=O groups)

wherein n has the meaning defined in Formula I in a dry aprotic solvent such as THF or DMF in the presence of a sterically hindered amine such as diisopropylethylamine with optional heating to give an intermediate of the formula $$St-OC-(CH_2)_n-COH \quad \text{Formula X}$$
(with two C=O groups)

which is activated by cooling to about −20° to −10° C. and reacting with isobutyl chloroformate in the presence of a tertiary amine, such as triethylamine for about 10–20 minutes during which time the reaction mixture is permitted to warm. To the activated derivative of Formula X is added an appropriate diamine of the formula $$RNH-(CH_2)_m NR_1R_2 \quad \text{Formula XI}$$

wherein m, R, $R_1$, and $R_2$ have the meanings defined in Formula I. This latter reaction is complete within an hour, and the product is isolated by standard procedures, e.g., extraction with an appropriate organic solvent, such as ethyl acetate and purified by crystallization and/or chromatography.

Alternatively in preparing the compounds of Formula I wherein Y is a bond and X is $$-\overset{O}{\underset{\|}{C}}N(R)-,$$

to the above obtained activated derivative of Formula X is added p-nitrophenol in the presence of a tertiary amine such as triethylamine to give a stabile intermediate of the formula $$StOC(CH_2)_n-\overset{O}{\underset{\|}{C}}-O-(C_6H_4)-NO_2 \quad \text{Formula XII}$$
(with C=O on left)

wherein St and n have the meanings defined in Formula I and ($C_6H_4$) is 1,4-phenylene. The intermediate of Formula XII is then reacted with a molar equivalent of an amine of Formula XI in a dipolar aprotic solvent such as THF or DMF in the presence of a base such as pyridine. The Formula I product is then isolated by extraction with an organic solvent, such as, ethyl acetate and purified by crystallization and/or chromatography.

To form acid addition salts of the compounds of Formulas I and II said compounds are treated with suitable pharmaceutically acceptable inorganic or organic acids by standard procedures. Suitable inorganic acids are, for example, hydrochloric, hydrobromic, nitric, sulfuric or phosphoric acids. Suitable organic acids include carboxylic acids, such as, acetic, propionic, glycolic, lactic, pyruvic, malonic, succinic, fumaric, malic, tartaric, citric, stearic, ascorbic, maleic, hydroxymaleic, benzoic, hydroxybenzoic, phenylacetic, glutomic, glutaric, cinnamic, salicylic, 2-phenoxybenzoic or sulfonic acids such as methane sulfonic, sulfonilic, toluenesulfonic, or 2-hydroxyethanesulfonic.

The quaternary ammonium salts of the compounds of Formulas I and II are formed by contacting said compounds with a suitable alkylating agent such as dimethyl sulfate, diethyl sulfate, or a suitable alkyl halide such as methyl or ethyl chloride or methyl or ethyl bromide or methyl or ethyl iodide.

The compounds of Formula III wherein X is $$-\overset{O}{\underset{\|}{C}}N(R)-$$

are prepared by heating to about 60° C. a suitable aliphatic lactone, such as, propiolactone, γ-butyrolactone, δ-valerolactone, ε-caprolactone, etc., as n in Formula I increases in length, with an equimolar amount of an aliphatic diamine of Formula XI in an aprotic solvent such as DMSO, DMF or THF to give the acyclic amide which is isolated by diluting the reaction mixture with acidified water, washing with an immiscible solvent, such as ethyl acetate and adjusting the pH to about 12. The product is extracted with an organic solvent such as ethyl acetate, and the solvent is removed under reduced pressure to give the amide. The amide is reacted with p-nitrophenylchloroformate in a dry aprotic solvent such as THF in the presence of pyridine and isolated by standard procedures to give the compounds of Formula III or used without isolation to form compounds of Formula I.

The compounds of Formula IIIA are prepared in a manner similar to that described hereinabove using an appropriate aliphatic lactone and piperazine or N-(lower)alkylpiperazine and reacting the resultant amide with p-nitrophenylchloroformate.

The compounds of Formula III wherein X is

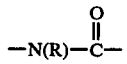

are prepared by reacting an appropriate N,N dialkyl amino alkanoic acid having an alkylene chain length of from 1 to 5 carbon atoms with a chloroformate ester, such as isobutyl chloroformate, in a dry chilled aprotic solvent, such as THF or DMF, in the presence of a tertiary amine to give the carboxylate-activated amino acid. This solution is then added dropwise with stirring to a second solution containing an equimolar amount of an amino alcohol of the formula HO—$(CH_2)_n$—NH(R) wherein n and R have the meanings defined in Formula I. An amide is obtained and any ester formed by reaction at the wrong end of the amino alcohol is eliminated by selective hydrolysis. The product is isolated by standard extractive methods, and the oily product is taken up in a dry aprotic solvent and treated with p-nitrophenylchloroformate in the presence of pyridine to give the compounds of Formula II which may be isolated by standard procedures.

The compounds of Formula III wherein X is oxy are prepared by reacting a suitable hydroxyalkoxyalkyl halide of the formula HO$(CH_2)_n$—O$(CH_2)_m$—halide wherein n and m have the meanings defined in Formula I and halide is, e.g., chloride or bromide with an amine of the formula $HNR_1R_2$ wherein $R_1$ and $R_2$ are as defined in Formula I in a dry aprotic solvent with a catalytic amount of NaI present to yield an amino alcohol. After purifying the amino alcohol by extractive methods, it is taken up in a dry aprotic solvent and reacted with p-nitrophenylchloroformate in the presence of pyridine to give a reactive mixed p-nitrophenyl carbonate ester of Formula III.

To prepare the compounds of Formula III wherein X is sulfur, an aliphatic ω-halo alcohol of the formula HO$(CH_2)_n$ halo wherein n is as defined in Formula I and halo is chloro or bromo is reacted with an aliphatic thiol of the formula HS$(CH_2)_m NR_1R_2$ wherein m, $R_1$ and $R_2$ are as defined in Formula I, to give a sulfide. The reaction is carried out in a partially aqueous solvent with a slight excess of NaOH and a reducing agent, e.g., sodium bisulfite, to inhibit disulfide formation. The product is isolated by extractive methods. This product may be oxidized at this stage to give a sulfoxide or sulfone if desired, or it may be maintained in the sulfide form. To form the sulfoxide, i.e., X is —S(O)—, the sulfide amino alcohol is treated with one equivalent of sodium metaperiodate in aqueous lower alcohol at 0° C. When oxidation is complete the sodium iodate is filtered out and the sulfoxide isolated by standard procedures. To form the sulfone, i.e., X is —S($O_2$)—, the sulfide amino alcohol is dissolved in a large excess of 90% formic acid and heated to about 70° C. for several minutes. After cooling to room temperature the solution is treated with 30% hydrogen peroxide. Oxidation proceeds through the sulfoxide to the sulfone. When the oxidation is complete, most of the formic acid is removed under reduced pressure, and the remaining residue is taken up in methanolic HCl. After one hour the mixture is concentrated under reduced pressure to give the desired sulfone-linked amino alcohol as the HCl salt. Final purification is achieved by recrystallization or by chromatography if needed. The sulfur-linked amino alcohol is then converted to a reactive mixed carbonate ester by combining it with an equimolar quantity of p-nitrophenylchloroformate in an aprotic solvent with added pyridine to give the compounds of Formula II which may be isolated by standard procedures.

To prepare the compounds of Formula IV wherein X is

an ω-haloalkyl$C_{2-9}$-carboxylic acid is reacted with equimolar quantities of triethylamine and isobutylchloroformate at −10° C. in an aprotic solvent, preferably THF. The solution is allowed to warm to room temperature and a diamine of the formula NH(R)$(CH_2)_m NR_1R_2$ wherein R, $R_1$, $R_2$ and m have the meanings defined in Formula I is added. After about 30 minutes the amide product is isolated by extractive procedures. This product is then reacted with an equimolar amount of thiourea in propylene glycol at an elevated temperature. When the halide has been displaced, the isothiouronium salt is cleaved by adding an amine such as tetraethylene pentamine and continuing to apply heat. When the free thiol was formed, this product is isolated by extractive means or by distillation under reduced pressure.

The compounds of Formula IVA are prepared in a manner similar to that described above only piperazine or N-(lower)alkylpiperazine is substituted for the diamine.

To prepare compounds of Formula IV wherein X is

an amino acid of the formula HOOC$(CH_2)_m NR_1R_2$ wherein m, $R_1$ and $R_2$ are as defined in Formula I is activated by reaction with isobutylchloroformate in a chilled dry aprotic solvent, such as THF, with sufficient triethylamine to take up the liberated HCl. This solution is allowed to warm to room temperature and is then added dropwise under nitrogen to a solution containing an amino alcohol of the formula HO$(CH_2)_n$NH(R) wherein n and R are as defined in Formula I. The amide thus obtained is purified by standard procedures. This amide is then dissolved in pyridine and is treated with methane sulfonyl chloride to give the terminal mesyl group. The pyridine is removed under reduced pressure, and the product is heated with a 10% molar excess of thiourea in propylene glycol. When the displacement of the mesyl group by thiourea is complete the resulting isothiouronium salt is cleaved by heating with added tetraethylenepentamine to give the compounds of Formula III which are isolated by extractive procedures or by distillation.

The compounds of Formula IV wherein X is oxy are prepared by reacting an N,N-dialkylamino alcohol of the formula HO$(CH_2)_m NR_1R_2$ wherein m, $R_1$ and $R_2$ are as defined in Formula I with an equimolar quantity of sodium hydride in DMF to form the sodium alkoxide. This solution is then added dropwise to a large molar excess of an aliphatic $C_{2-9}$ dihalide or a dimesylate in DMF. If the halogen groups are chloride, sodium iodide is added as a catalyst. When ether formation is complete, the desired mono ether is isolated by extractive procedures then treated with thiourea in refluxing 95% ethanol to yield the isothiouronium salt. This salt is cleaved by treating the solution with a slight molar excess of sodium hydroxide solution and continuing to reflux the mixture under nitrogen. The amino thiol is then isolated from the reaction mixture by extractive procedures to give the compounds of Formula IV.

The compounds of Formula IV wherein X is sulfur are prepared as follows. An N,N-dialkylamino thiol of the formula $HS(CH_2)_mNR_1R_2$ wherein m, $R_1$ and $R_2$ are as defined in Formula I is dissolved in a lower alcohol and treated with a slight molar excess of NaOH. This solution is then added dropwise to a large molar excess of a dibromide of the formula $Br(CH_2)_nBr$ wherein n is an integer of from 2 to 9, in an aprotic solvent such as DMF or THF. The desired mono-sulfide is isolated by standard extractive procedures. At this stage, the sulfide could be oxidized, if desired, to give either the sulfoxide or the sulfone. To prepare the compounds of Formula IV wherein X is sulfoxide the sulfide obtained above is treated with sodium metaperiodate in a lower aqueous alcohol by procedures analogous to those described hereinabove in connection with the preparation of compounds of Formula II. To prepare the compounds of Formula IV wherein X is sulfone the sulfide is dissolved in glacial acetic acid and treated with 30% hydrogen peroxide thus oxidizing the sulfide through the sulfoxide to the sulfone. Whether or not further oxidation is elected, the subsequent steps are the same. The sulfur-linked amino bromide is treated with an equimolar amount of thiourea in refluxing 95% ethanol to yield an isothiouronium salt. This salt is cleaved by the addition of concentrated base to yield the free thiolate. Upon acidification and extractive workup the compounds of Formula IV are obtained.

The steroid chloroformates of Formula V are prepared by reacting the parent 21 hydroxy steroid with a molar excess of phosgene in THF in a chilled reaction vessel which is then allowed to warm to room temperature. After about one hour the solution is concentrated under reduced pressure and the chloroformate precipitates out.

The compounds of Formula VI wherein X is

are prepared by reacting an aminoacid of the formula $HN(R)(CH_2)_n$—COOH with a bromoalkanoyl chloride wherein the alkanoyl moiety contains from 2 to 6 carbon atoms in an aqueous solvent at a pH of about 10 after which the pH is adjusted to about 3. The thus formed amide is extracted with an organic solvent such as ethyl acetate and isolated by procedures generally known in the art then taken up in an aprotic solvent such as THF or DMF and treated with an amine of the formula $HNR_1R_2$ wherein $R_1$ and $R_2$ have the meanings defined in Formula I to give the compounds of Formula VI which are isolated by standard procedures.

The compounds of Formula VI wherein X is

are prepared by reacting an appropriate alkylene dicarboxylic acid with an appropriate alkylenediamine by procedures well known in the art.

The compounds of Formula VI wherein X is oxy are prepared as follows. A t-butyl ester of a carboxylic acid of the formula

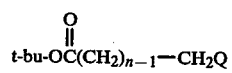

wherein n is as defined in Formula I and Q is a leaving group such as chloro, bromo, iodo, O-mesyl or O-tosyl is treated with an ω-hydroxy amine of the formula $HO(CH_2)_mNR_1R_2$ wherein m, $R_1$ and $R_2$ are as defined in Formula I, e.g., 2-diethylamino ethanol, and an equimolar amount of a strong non-nucleophilic base, e.g., potassium t-butoxide, in a dry aprotic solvent, e.g., THF, to yield the ether coupled promoiety. If the displaceable group is chloro or bromo, NaI may be added as a catalyst. When the ether formation is complete the product is isolated by extractive methods. The t-butyl ester is hydrolyzed by treatment with toluene sulfonic acid in an organic solvent, e.g., toluene, or with anhydrous trifluoroacetic acid to give the compounds of Formula V.

The compounds of Formula VI wherein X is sulfur are prepared by reaction of an ω-mercaptocarboxylic acid of the formula $HOOC(CH_2)_nSH$ and an ω-halo amine of the formula $halo(CH_2)_mNR_1R_2$ wherein n, m, $R_1$ and $R_2$ are as defined in Formula I and halo is chloro or bromo, in aqueous base containing a reducing agent, such as $K_2S_2O_5$. The pH is maintained at 10–12 by addition of base if necessary. A water miscible organic solvent, such as THF, may be added if required to solubilize the ω-halo-amine. When the reaction is complete the sulfide is isolated by extractive methods to give the compounds of Formula V.

The compounds of Formula VI wherein X is sulfoxide are obtained by treating the corresponding Formula VI compound wherein X is sulfur with sodium periodate in a lower aqueous alcohol as described hereinabove. The compounds of Formula VI wherein X is sulfone are obtained by treating the corresponding sulfur compound with hydrogen peroxide in 50% acetic acid by procedures analogous to those described hereinbefore.

The compounds of Formulas VII and VIII are prepared by general procedures well known in the art. The bis-acids of Formula IX and the alkylenediamines of Formula XI are known in the art or are prepared by means well known in the art.

The ω-mercaptocarboxylic acids employed hereinabove are obtained by treating an acid of the formula $HOOC(CH_2)_nQ$ wherein Q is chloro, bromo, iodo, O-mesyl or O-tosyl and n is 2 to 9 with thiourea in a refluxing lower alcohol to give the isothiouronium salt which is subsequently cleaved by addition of aqueous base under reducing conditions to give the free thiol group.

The ω-haloamines employed hereinabove wherein m is other than 2 are obtained by adding a secondary amine of the formula $HNR_1R_2$ wherein $R_1$ and $R_2$ are as defined in Formula I portionwise to a molar excess of an appropriate α,ω-alkylenedihalide. Generally the reaction mixture is heated and if the halide is chloride, an iodide salt may be added as a catalyst. The ω-haloamines wherein m is 2 are commercially available.

The following examples further illustrate the invention.

EXAMPLE 1

(a) Methylprednisolone 21-hemisuberate

To a solution of 17.6 g octanedioic acid (0.1 mole) and 17.5 ml diisopropylethylamine (0.1 mole) in 100 ml DMF was added a DMF solution (50 ml) containing 10 g of methylprednisolone 21-iodide (0.02 mole). The reaction mixture was allowed to stand at room temperature overnight after which the reaction mixture was concentrated under reduced pressure (50° C.) and dissolved in ethyl acetate (500 ml). Repeated extractions with water (500 ml) adjusting the biphasic mixture to pH 6.0 (dilute NaOH) were carried out until the final pH of the aqueous phase remained constant. This procedure removed excess amine and dicarboxylic acid. The organic layer was evaporated in vacuo leaving an off-white solid residue which was redissolved in hot acetone-methanol and recrystallized after addition of hexane, m.p. 188°–191° C.

(b) N,N,N'-Trimethylethylenediamine amide of methylprednisolone 21-hemisuberate (HCl salt)

A THF solution (10 ml) containing 0.65 g (1.2 mmol) of the product of Example 1(a) and 0.2 ml triethylamine (1.4 mmol) in a 3-neck flask flushed with $N_2$ and immersed in a dry ice-isopropanol bath was treated with 0.18 ml of isobutylchloroformate (1.4 mmol). The flask was allowed to warm to room temperature. Within 15 minutes, a white precipitate (triethylamine HCl) had formed, after which 0.18 ml (1.4 mmol) N,N,N'-trimethylethylenediamine was added. The reaction appeared to reach completion (>90%) within 5 minutes.

To the reaction mixture was added ethyl acetate (100 ml) and 150 ml water adjusting the pH of the aqueous phase to 2–2.5 with 0.1N HCl (rapid stirring). The first aqueous extract removed product nearly quantitatively. This solution was washed with 20 ml ethylacetate.

After the addition of 75 ml ethylacetate the pH was adjusted to 7.5 (dilute NaOH) with rapid stirring resulting in nearly quantitative extraction of product. The organic solvent from a second extract was combined with the first, water was partially removed ($Na_2SO_4$), and the filtered solution was concentrated to an oil under reduced pressure.

The oil residue was dissolved in THF and titrated with 0.1N HCl to an end point at an apparent pH of 2.6. Solvent was removed in vacuo removing residual water with an acetonitrile azeotrope. Addition of butyl chloride to the oil residue resulted in formation of a white crystalline solid which was stirred in the solvent for approximately one week. This material was recrystallized from isopropyl alcohol-butyl chloride and dried at 55° C. high vacuum overnight to give the title compound, m.p. 166°–167.5° C.

EXAMPLE 2

N,N-Diethylethylenediamine amide of methylprednisolone 21-hemisuberate (HCl salt)

A THF solution (150 ml) containing 7.6 g (14.3 mmol) of methylprednisolone 21-hemisuberate and 2.2 g (16 mmol) of triethylamine in a nitrogen flushed flask immersed in a dry ice-acetone bath was treated with 2.1 ml (16 mmol) of isobutylchloroformate. The flask was allowed to warm to room temperature while maintaining constant stirring. Within 15 minutes, a white precipitate had formed (triethylammonium chloride), after which 2.25 ml (16 mmol) of N,N-diethylethylenediamine was added. Product formation, monitored by thin layer chromatography (tlc) (silica gel; ethylacetate/methanol/$NH_4OH$, 20/4/1), appeared to reach 80% of theory within an hour.

The reaction mixture was concentrated under vacuum to an oil, taken up in 400 ml ethyl acetate, and extracted with 400 ml dilute HCl. The organic phase was reextracted with 100 ml dilute HCl and the combined aqueous phases were washed with 100 ml ethyl acetate. The acidic aqueous extract was then stirred with 400 ml ethyl acetate while adjusting the pH to 7.7 with 1N NaOH. A second organic extract of the aqueous phase (again adjusted to pH 7.7) was combined with the first, and the resulting solution was concentrated to an oil. The oil was taken up in THF and titrated with 24.7 ml of 1N HCl. Solvent was removed under vacuum and residual water was removed as an azeotrope with acetonitrile. Trituration of the semisolid product overnight with ethyl ether produced 7.7 g of a free flowing white solid. This solid was recrystallized from acetonitrile to give, after drying at 60° under high vacuum, 6.6 g of crystalline solid.

Analysis: $C_{36}H_{56}N_2O_7 \cdot HCl$. Calculated: C, 64.99; H, 8.64; N, 4.21; Cl, 5.33. Found: C, 64.67; H, 8.41; N, 4.14; Cl, 5.37. $KF(H_2O)$: 0.14%. M.P.: 160°–175° C. (a sample recrystallized from isopropanol and butylchloride melted at 160°–161.5°).

EXAMPLE 3

N,N,N'-Triethylethylenediamine amide of methylprednisolone 21-hemisuberate (HCl salt)

A THF solution (50 ml) containing 3.7 g (7 mmol) methylprednisolone hemisuberate and 1.15 ml (8 mmol) of triethylamine in a nitrogen purged flask chilled with dry ice-acetone was treated with 1.05 ml (8 mmol) isobutylchloroformate. The reaction mixture was allowed to come to room temperature during which time (15 minutes) a white precipitate formed. Next, 1.43 ml (8 mmol) of N,N,N'-Trimethylethylenediamine was added. The reaction, monitored by thin layer chromatography, appeared to be complete after about 5 minutes.

The usual extractive work-up was done, extracting the product first into dilute HCl and then into ethyl acetate from a pH 7.5 aqueous phase. After the ethyl acetate solution of the free base was concentrated under vacuum, the oily residue was taken up in THF and converted to the salt by titration with 1N HCl. The product was then stripped of solvent, triturated several days with ethyl ether, dissolved in water, and freeze dried yielding a white amorphous powder which was further purified by chromatography and freeze dried yielding a white powder which was equilibrated with lab air to give the title product.

Analysis: $C_{38}H_{60}N_2O_7 \cdot HCl \cdot 1(H_2O)$. Calculated: C, 64.16; H, 8.93; N, 3.94; Cl, 4.98. Found: C, 64.22; H, 8.96; N, 3.93; Cl, 5.02. $KF(H_2O)$: Calculated: 2.53%. Found: 2.40%. HPLC: (243λ uv detector): >99% apparent purity.

EXAMPLE 4

N,N,N'-Trimethylethylenediamine amide of methylprednisolone 21-hemisuccinate A THF solution (15 ml) containing 2.4 g (5 mmol) of methylprednisolone hemisuccinate and 0.8 ml (5.7 mmol) of triethylamine in a nitrogen purged flask immersed in a dry ice-isopropanol bath was treated with 0.75 ml (5.7 mmol) of isobutylchloroformate. The flask was allowed to warm to room temperature. After 15 minutes, 0.7 ml (5.6 mmol) of N,N,N'-trimethylethylenediamine in 20 ml THF was added, and stirring was continued for one hour. The reaction mixture was first diluted with 100 ml ethyl acetate and extracted with dilute HCl. The aqueous phase was washed two more times with ethyl acetate and was then stirred with 100 ml fresh ethyl acetate while adjusting the pH to 8.0 with 1N NaOH. Three extractions were done at pH 8, after which the combined organic extracts were dried over $Na_2SO_4$ and concentrated to an oil. Residual water was removed by means of the acetonitrile azeotrope. The gummy product was taken up in 15 ml of ethyl acetate from which it slowly crystallized. The white crystalline solid was dried at 60° under high vacuum to give the title compound.

Analysis: $C_{31}H_{46}N_2O_7$. Calculated: C, 66.64; H, 8.30; N, 5.01. Found: C, 66.70; H, 8.29; N, 4.80. $KF(H_2O)$: 0.23%. M.P.: 180.1°–181.6° C. HPLC: (254 uv detector) >99% apparent purity.

EXAMPLE 5

(a) Methylprednisolone 21-hemiadipate

A mixture of 5 g of 21-iodo-methylprednisolone, 14.6 g adipic acid, and 34.8 ml diisopropylethylamine in 45 ml DMF and 20 ml acetone was permitted to stand at 25° C. for 60 minutes with occasional stirring. The reaction mixture was dissolved in 250 ml ethyl acetate, extracted with 3 portions of 0.08M citric acid solution, then twice with equal volumes of aqueous NaOH adjusted to pH 10. Without delay the combined basic aqueous extracts were acidified to pH 5 and extracted twice with equal volumes of ethyl acetate. The combined organic layers were washed twice with water and solvent was removed on a rotary evaporator to give the title product which was recrystallized twice from ethyl acetate/hexane.

Silica gel TLC: single spot at RF=0.65 (15:5:2:1 $CH_2Cl_2$/EtOAc/HOAc/MeOH). Analysis: $C_{28}H_{38}O_8$. Theory: C, 66.92; H, 7.62. Found: C, 67.01; H, 7.91. M.P.: 164.3°–165.6° C.

(b) N,N,N'-Trimethylethylenediamine amide of methylprednisolone 21-hemiadipate (HCl salt)

A stirred solution of 3.52 g (7 mmol) methylprednisolone hemiadipate and 1.11 ml (8 mmol) triethylamine in 100 ml THF contained in a flask purged with nitrogen and cooled in a dry ice-acetone bath was treated with 1.05 ml (8 mmol) isobutylchloroformate. The solution was allowed to warm to room temperature for 20 minutes during which time a precipitate of triethylamine hydrochloride formed and to which 1.1 ml (8 mmol) of N,N,N'-trimethylethylenediamine was then added.

After one hour the solvent was removed under reduced pressure and the remaining oil was partitioned between 250 ml dilute HCl and 250 ml ethyl acetate. The aqueous phase was collected and adjusted to pH 8.2 with 1N NaOH while stirring with 250 ml fresh ethyl acetate. After one more extraction from pH 8 water, the combined organic phases were dried with $MgSO_4$ and concentrated to an oil. The oil was then taken up in THF and titrated with 1N HCl. After stripping solvent from the titrated solution and removing water by means of an acetonitrile azeotrope, the gummy product was triturated several days with ethyl ether. 4.0 g (91% yield) of a white free flowing solid was obtained. Numerous methods of recrystallization were tried unsuccessfully. The ether solid was finally dried at 60° C. under vacuum then equilibrated with lab air.

$KF(H_2O)$: 3.18%. TLC: (Silica gel; ethyl acetate/methanol/$NH_4OH$, 20/4/1; developed by charring with $(NH_4)_2SO_4$): single spot at rf=0.56. HPLC: (243λ uv detector): >99% apparent purity.

EXAMPLE 6

N,N,N'-Triethylethylenediamine amide of methylprednisolone 21-hemiadipate (HCl salt)

A THF solution (50 ml) containing 2.5 g (5 mmol) methylprednisolone 21-hemiadipate and 0.79 ml (5.7 mmol) triethylamine, stirred in a nitrogen purged flask and chilled with dry ice-acetone, was treated with 0.72 ml (5.5 mmol) of isobutylchloroformate. The flask was allowed to warm to room temperature for 15 minutes while a precipitate of triethylamine hydrochloride formed. The solution was then treated with 0.98 ml (5.5 mmol) of N,N,N'-triethylethylenediamine and stirred for 30 minutes. The reaction mixture was worked up in a manner similar to that described in Example 5, partitioning first from ethyl acetate into pH 2 water then out of pH 8 water into ethyl acetate. The solvent was stripped under vacuum leaving an oil which was then dissolved in THF and titrated with 1N HCl. The solvent was again removed, using acetonitrile to remove all water as the azeotrope. The remaining gum was triturated overnight in ethyl ether yielding 3 g (90% yield) of a free flowing white solid. The solid resisted attempts to recrystallize it and was finally taken up in water and freeze dried. The lyophilized solid was dried at 60° under vacuum and equilibrated with lab air to give the title compound.

$KF(H_2O)$: 1.63%. TLC: (Silica gel; ethyl acetate/methanol/$NH_4OH$, 20/4/1; developed by charring with $(NH_4)_2SO_4$): one spot rf=0.71. HPLC: (243λ uv detector) >99% apparent purity.

EXAMPLE 7

(a) N,N-Diethylaminopropionylamide of methylprednisolone 21-aminocaproate

To a stirred solution of 6.5 g (50 mMol) of aminocaproic acid in 30 ml of water, pH 10.5, was added dropwise 2 ml (20 mMol) of bromopropionylchloride to give a homogenous solution. The pH of the solution was adjusted to 3 and extracted repeatedly with ethyl acetate. The ethyl acetate solution was concentrated to an oil and purified by silica gel chromatography using ethyl acetate and 2% acetic acid as the mobil phase. The product fraction was stripped of solvent leaving an oil consisting of 12 mMol (by titration) of 6-(3-bromopropionylamino)caproic acid.

(b) The acid product obtained above was dissolved in 50 ml DMF and 20 ml of diethylamine. After 3 weeks at room temperature the solvent was removed and the oil was taken up in water. After adjusting to pH 12 with NaOH the water was evaporated off and the residue was again taken up in water. After adjusting to pH 2.5 with HCl, acetonitrile was added to precipitate inorganic salts (NaBr, NaCl). Attempts to obtain solid product from the filtrate were not successful, so solvent was simply removed to give 6-(3-diethylaminopropionylamino)caproic acid as an oil that was >90% pure by titration.

(c) The amino acid product obtained above was dissolved in 30 ml dry DMF to which was added 2 ml (11.5 mMol) of diisopropylethylamine and 4.84 g (10 mMol) of 21-iodo-6α-methylprednisolone. After 2 hours at room temperature a second 10 mMol aliquot of 21-iodo methylprednisolone was added and the mixture was heated to 65° for 2 hours. Extraction between ethyl acetate and dilute HCl effectively removed most of the unwanted components, leaving the desired product in the aqueous phase. After adjusting to pH 8, the product was extracted into ethyl acetate and concentrated to an oil and chromatographed on silica gel (90:8:1, ethyl acetate:methanol:triethylamine). Product fractions were stripped of solvent, the remaining oil was taken up in THF/H$_2$O, and the solution was tritrated using 3.5 ml of 1N HCl. Solvent was removed and final crystallization of the oil from isopropanol gave the title compound as a pure white crystalline solid.

Analysis for C$_{35}$H$_{54}$N$_2$O$_7$·HCl. Calculated (corrected for 0.83% H$_2$O): C, 64.01; H, 8.67; N, 4.26; Cl, 5.39. Found: C, 63.56; H, 8.31; N, 4.15; Cl, 5.44. M.P.: 210.1°–211.0° C.

EXAMPLE 8

Hydrocortisone,21-[6-[[2-(diethylamino)propyl]amino]-6-oxo-hexyl carbonate], hydrochloride 5.5 ml of ε-caprolactone is refluxed with 8 ml of N,N-diethyl-1,3 propanediamine in 50 ml of dry THF to form the ω-amido caproic acid. The product is isolated by diluting the reaction mixture with acidified water, washing the solution with ethyl acetate, adjusting the pH up to 10–12, extracting the product into ethyl acetate, and concentrating this solution under reduced pressure. The compound thus obtained is then treated with 10 g of p-nitrophenylchloroformate in 100 ml of THF containing 4 ml of pyridine. When the chloroformate is all consumed, the solution is reacted with 15 g of hydrocortisone, 3.4 ml of pyridine, and 1 g of DMAP, and the resulting solution is heated until the reactants are consumed. The reaction mixture is then concentrated under reduced pressure and partitioned between ethylacetate and water adjusted to pH 2–3. The aqueous phase is adjusted to pH 7 and extracted with ethylacetate to isolate the desired product. Final purification is accomplished by chromatography and/or crystallization. The hydrochloride salt is obtained by dissolving the free base in 1/1 THF/water and titrating with dilute hydrochloric acid.

EXAMPLE 9

Dexamethasone,21-[6-[[2-(diethylamino)ethyl]ethyl amino]-6-oxo-hexyl thiocarbonate], hydrochloride 9.75 g of 6-bromohexanoic acid is dissolved in 150 ml of dry THF in a three-neck flask fitted with a nitrogen line and a drying tube. With the reaction vessel chilled to about −10° C., 7.0 ml of triethylamine and 6.5 ml of isobutylchloroformate are added and the resultant solution is allowed to warm to ambient temperature while stirring. After about 15 minutes, 8.9 ml of N,N,N'-triethylethylenediamine is added. The mixture is stirred for about 30 minutes then concentrated under reduced pressure and diluted with water adjusted to about pH 3. The aqueous solution is first washed with ethylacetate then adjusted to a pH of about 9 and extracted with ethylacetate. The latter ethylacetate extract is concentrated to an oil under reduced pressure then dissolved in 50 ml of propylene glycol. This solution is then treated with 3.8 g of thiourea with heating and vigorous stirring. When the reaction is complete, 5 ml of tetraethylenepentamine is added to the solution and heating is continued until the isothiouronium salt is all converted to the thiol. The thiol is isolated by diluting the reaction mixture with 500 ml of water adjusted to pH 3, washing this solution with ethylacetate, adjusting the pH up to 9, and extracting thiol into ethylacetate. The solvent is removed under reduced pressure before the coupling step.

The appropriate steroid chloroformate is prepared by dissolving 10 g of dexamethasone in 100 ml of THF and treating this solution with 10 ml of phosgene while cooling in a dry-ice acetone bath. The reaction vessel is allowed to come to room temperature, venting excess phosgene through a sodium hydroxide trap, and after one hour the solution is concentrated under reduced pressure to about 30 ml. The dexamethasone 21-chloroformate is isolated by filtration after it crystallizes out of solution. The final coupling reaction is accomplished by heating the above-obtained thiol with the chloroformate in THF under nitrogen. The title product is isolated by extractive procedures. It is most convenient to purify the product as the hydrochloride salt.

EXAMPLE 10

Methylprednisolone,21-[5-[[2-(diisopropylamino)ethyl]thio]pentanoate]hydrochloride (a) 13.6 g of 5-bromovaleric acid is refluxed in 95% ethanol with 6 g of thiourea to form an ω-isothiouronium salt. The isothiouronium group is cleaved by adding 40 ml of 4N NaOH solution and heating under a nitrogen atmosphere. The ω-mercaptovaleric acid is isolated by extractive procedures, and 5.0 g of said acid is reacted with 7 g of diisopropylaminoethyl chloride hydrochloride in 105 ml of 1N Na$_2$CO$_3$ in the presence of 0.5 g of sodium bisulfite. The sulfide coupled dialkylamino acid product is isolated by extractive methods.

(b) To form the ester linkage, 5 g of the above obtained sulfide-coupled dialkylamino acid is heated with a solution of 9.0 g of 21-iodo-methylprednisolone in 30 ml of dry DMF containing 3.5 ml of diisopropylethylamine. The ester product is isolated by extractive procedures. Final purification is accomplished by chromatography and/or crystallization. The hydrochloride is formed by titrating the product in aqueous THF with dilute hydrochloric acid.

EXAMPLE 11

Methylprednisolone,21-[5-[[2-(diisopropylamino)ethyl]sulfinyl]pentanoate], hydrochloride In 100 ml of 50% ethanol cooled to 0° C. 6.5 g of the sulfide is treated with 2.2 g of sodium metaperiodate. When the reaction is complete, the sodium iodate is removed by filtration and the sulfoxide product isolated by standard methods. Final purification is accomplished by chromatography and/or crystallization. Conversion to the hydrochloride salt is effected by titration of the free base is aqueous THF with hydrochloric acid.

EXAMPLE 12

Methylprednisolone,21-[5-[[2-(diisopropylamino)ethyl]sulfonyl]pentanoate], hydrochloride The title compound is prepared in a manner corresponding to that described for the product of Example 10, except that an oxidation step is included prior to forming the ester linkage. The sulfide-coupled dialkylamino acid obtained as in Example 10(a) is oxidized by dissolving 4.9 g of said acid in 40 ml of 50% acetic acid and adding 5 ml of 30% hydrogen peroxide. When the sulfide is oxidized all the way to the sulfone, the product is isolated by simple concentration under reduced pressure followed by chromatography and/or crystallization. This sulfone-coupled compound is then used to form an ester bond with the steroid as described in Example 11(b).

EXAMPLE 13

Methylprednisolone,21-[6-(2-morpholino ethoxy)hexanoate], hydrochloride

To a solution of 6.1 g of N-$\beta$-hydroxyethylmorpholine in 100 ml of dry THF containing 5.7 g of potassium t-butoxide is added 12.6 g of the t-butyl ester of 6-bromohexanoic acid (produced by treatment of the acid with isobutene and sulfuric acid). When ether formation is complete, the $\omega$-morpholino ester is isolated by extractive procedures. The free acid is obtained by refluxing 8.8 g of the morpholino ester in 100 ml of methylene chloride in the presence of 1 ml of trifluoroacetic acid. After isolating the $\omega$-morpholine acid by standard procedures, it is dissolved in 80 ml of DMF and heated to 60°-70° C. with 11.3 g of methylprednisolone 21-mesylate plus 4.4 ml of N,N-diisopropylethylamine. The ester product is isolated by extractive procedures, and the final purification is accomplished by chromatography and/or crystallization. Conversion to the hydrochloride salt is effected by dissolving the free base in aqueous THF and titrating with dilute hydrochloric acid.

EXAMPLE 14

(a) Methylprednisolone 21-hemisuberate

In a solution of 17.6 g octanedioic acid (0.1 mole) and 17.5 ml diisopropylethylamine (0.1 mole) in 100 ml dimethylformamide (DMF) was added a DMF solution (50 ml) containing 10 g of methylprednisolone 21-iodide (0.02 mole). The reaction mixture was allowed to stand at room temperature overnight after which the reaction mixture was concentrated under reduced pressure (50° C.) and dissolved in ethyl acetate (500 ml). Repeated extractions with water (500 ml) adjusting the biphasic mixture to pH 6.0 (dilute NaOH) were carried out until the final pH of the aqueous phase remained constant. This procedure removed excess amine and dicarboxylic acid. The organic layer was evaporated in vacuo leaving an off-white solid residue which was redissolved in hot acetone-methanol and recrystallized after addition of hexane, m.p. 188°-191° C.

(b)
Methylprednisolone,21-[2-(4-methylpiperazino-8-oxo-octanoate], monohydrochloride To a solution of 5.3 g (10 mMol) methylprednisolone hemisuberate in 100 ml dry THF was added 1.4 ml (10 mMol) triethylamine. The mixture was cooled to about −60° C. under nitrogen and 1.3 ml (10 mMol) of isobutylchloroformate was added. The mixture was allowed to warm to 10°-20° C. over about 12 minutes after which 1.22 ml (11 mMol) N-methyl piperazine was added. After about one hour the reaction mixture was partitioned between dilute HCl and ethyl acetate. The aqueous layer was adjusted to pH 7.5 while stirring with fresh ethyl acetate and the organic layer was separated, dried (MgSO$_4$), filtered, and solvent was removed on a rotary evaporator. The oil residue was dissolved in 100 ml THF and 10 ml H$_2$O and titrated with 1N HCl to an end point. After removal of solvent the resulting viscous oil was triturated overnight in ether to yield 4.4 g white solid which was dissolved in water, washed with ethyl acetate, and the pH was adjusted to 7.6 with 0.5N NaOH while stirring with fresh ethyl acetate. The ethyl acetate was collected, dried over MgSO$_4$, filtered and evaporated to an oil which was triturated in acetonitrile to yield 2 g white crystalline solid (needles). This highly pure material was again acidified (aqueous HCl), solvent was removed, and the gummy residue was triturated in 100 ml acetonitrile several days to yield 2 g white crystalline solid. This material was dried at 55° C. under high vacuum and equilibrated with laboratory atmosphere to give the title compound.

Analysis for C$_{35}$H$_{53}$N$_2$O$_7$Cl. Calculated (corrected for 5.1% H$_2$O): C, 64.75; H, 8.23; N, 4.31; Cl, 5.46. Found: C, 64.84; H, 7.72; N, 4.34; Cl, 5.55. M.P.: 181.2°-185.0° C.

EXAMPLE 15

When in the procedure of Example 1(a) an appropriate amount of the 21-iodide of triamcinolone, dexamethasone, betamethasone, flurandrenolone, prednisone, fluprednisolone, hydrocortisone, cortisone, corticosterone, dehydrocorticosterone, prednisolone, flumethasone, 11-deoxycorticosterone, 9$\alpha$-fluorohydrocortisone, chlorprednisolone or paramethasone is substituted for methylprednisolone 21-iodide the following intermediates are obtained:

triamcinolone 21-hemisuberate,
dexamethasone 21-hemisuberate,
betamethasone 21-hemisuberate,
flurandrenolone 21-hemisuberate,
prednisone 21-hemisuberate,
fluprednisolone 21-hemisuberate,
hydrocortisone 21-hemisuberate,
cortisone 21-hemisuberate,
corticosterone 21-hemisuberate,
dehydrocorticosterone 21-hemisuberate,
prednisolone 21-hemisuberate,
flumethasone 21-hemisuberate,
11-deoxycorticosterone 21-hemisuberate,
9$\alpha$-fluorohydrocortisone 21-hemisuberate,
chlorprednisolone 21-hemisuberate,
paramethasone 21-hemisuberate.

When in the procedure of Example 3 an appropriate amount of each of the above obtained intermediates is substituted for methylprednisolone hemisuberate the following respective products are obtained:

N,N,N'-trimethylethylenediamine amide of triamcinolone 21-hemisuberate.HCl,
N,N,N'-trimethylethylenediamine amide of dexamethasone 21-hemisuberate.HCl,
N,N,N'-trimethylethylenediamine amide of betamethasone 21-hemisuberate.HCl,
N,N,N'-trimethylethylenediamine amide of flurandrenolone 21-hemisuberate.HCl, N,N,N'-trimethylethylenediamine amide of prednisone 21-hemisuberate.HCl,
N,N,N'-trimethylethylenediamine amide of fluprednisolone 21-hemisuberate.HCl,
N,N,N'-trimethylethylenediamine amide of hydrocortisone 21-hemisuberate.HCl,
N,N,N'-trimethylethylenediamine amide of cortisone 21-hemisuberate.HCl,
N,N,N'-trimethylethylenediamine amide of corticosterone 21-hemisuberate.HCl,
N,N,N'-trimethylethylenediamine amide of dehydrocorticosterone 21-hemisuberate.HCl,
N,N,N'-trimethylethylenediamine amide of prednisolone 21-hemisuberate.HCl,
N,N,N'-trimethylethylenediamine amide of flumethasone 21-hemisuberate.HCl,
N,N,N'-trimethylethylenediamine amide of 11-deoxycorticosterone 21-hemisuberate.HCl,
N,N,N'-trimethylethylenediamine amide of 9α-fluorohydrocortisone 21-hemisuberate.HCl,
N,N,N'-trimethylethylenediamine amide of chlorprednisolone 21-hemisuberate.HCl,
N,N,N'-trimethylethylenediamine amide of paramethasone 21-hemisuberate.HCl.

EXAMPLE 16

When in the procedure of Example 8 an appropriate amount of N,N-diethyl-1,4-butanediamine is substituted for N,N-diethyl-1,3-propanediamine, and an appropriate amount of triamcinolone, dexamethasone, methylprednisolone, betamethasone, flurandrenolone, prednisone, fluprednisolone, cortisone or paramethasone is substituted for hydrocortisone the following respective products are obtained.

triamcinolone, 21-[6-[[2-diethylamino)butyl]amino]-6-oxo-hexylcarbonate,
dexamethasone, 21-[6-[[2-diethylamino)butyl]amino]-6-oxo-hexylcarbonate,
betamethasone, 21-[6-[[2-diethylamino)butyl]amino]-6-oxo-hexylcarbonate,
flurandrenolone, 21-[6-[[2-diethylamino)butyl]amino]-6-oxo-hexylcarbonate,
prednisone, 21-[6-[[2-diethylamino)butyl]amino]-6-oxo-hexylcarbonate,
fluprednisolone, 21-[6-[[2-diethylamino)butyl]amino]-6-oxo-hexylcarbonate,
methylprednisolone, 21-[6-[[2-diethylamino)butyl]amino]-6-oxo-hexylcarbonate,
cortisone, 21-[6-[[2-diethylamino)butyl]amino]-6-oxo-hexylcarbonate,
paramethasone, 21-[6-[[2-diethylamino)butyl]amino]-6-oxo-hexylcarbonate.

EXAMPLE 17

When in the procedure of Example 9 an appropriate amount of N,N-diethylethylenediamine is substituted for N,N,N'-triethylethylenediamine and an appropriate amount of hydrocortisone, methylprednisolone, triamcinolone, betamethasone, flurandrenolone, prednisone, fluprednisolone, cortisone or paramethasone is substituted for dexamethasone the following respective products are obtained:

triamcinolone, 21-[6-[[2-aminoethyl]-amino]-6-oxo-hexyl thiocarbonate,
betamethasone, 21-[6-[[2-aminoethyl]amino]-6-oxo-hexyl thiocarbonate,
flurandrenolone, 21-[6-[[2-aminoethyl]amino]-6-oxo-hexyl thiocarbonate,
prednisone, 21-[6-[[2-aminoethyl]amino]-6-oxo-hexyl thiocarbonate,
fluprednisolone, 21-[6-[[2-aminoethyl]amino]-6-oxo-hexyl thiocarbonate,
cortisone, 21-[6-[[2-aminoethyl]amino]-6-oxo-hexyl thiocarbonate,
paramethasone, 21-[6-[[2-aminoethyl]amino]-6-oxo-hexyl thiocarbomate,
hydrocortisone, 21-[6-[[2-aminoethyl]amino]-6-oxo-hexyl thiocarbonate,
methylprednisolone, 21-[6-[[2-aminoethyl]amino]-6-oxo-hexyl thiocarbonate.

The following examples are illustrative of typical formulations of representative compounds of the present invention.

EXAMPLE 18

| | |
|---|---|
| N,N,N'—Trimethylethylenediamine amide of hydrocortisone 21-succinate (HCl salt) | 49.0 mg |
| (Equivalent to 100 mg hydrocortisone) | |
| Dilute NaOH to adjust pH to 4.5 | |
| Sterile water for injection to make 1 ml | |

EXAMPLE 19

| | |
|---|---|
| N,N,N'—Triethylethylenediamine amide of methylprednisolone 21-suberate (HCl salt) | 185.0 mg |
| (Equivalent to 100 mg methylprednisolone) | |
| Acetic acid | 2.3 mg |
| Sodium acetate | 2.0 mg |
| Benzyl alcohol | 1.8 mg |
| HCl (dilute) or NaOH (dilute) to adjust pH to 4.25 | |
| Sterile water for injection to make 1 ml | |

EXAMPLE 20

| | |
|---|---|
| N,N—Diethylaminopropionylamide of dexamethasone 21-amino caproate | 25.0 mg |
| (Equivalent to 20 mg dexamethasone) | |
| Creatinine | 1.0 mg |
| Acetic acid | 4.6 mg |
| Sodium acetate | 2.0 mg |
| Sodium bisulfite | .0 mg |
| Disodium edetate | 1 mg |
| Methylparaben | .5 mg |
| Propylparaben | 2 mg |
| HCl (dilute) or NaOH (dilute) to adjust pH to 4.25 | |
| Water for injection to make 1 ml | |

FORMULA CHART

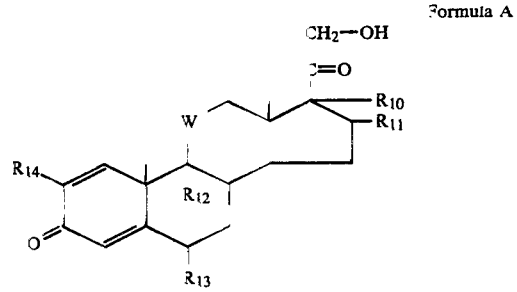

Formula A

In the above Formula A:
W is

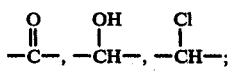

$R_{10}$ is H, α—OH;
$R_{11}$ is H, α—CH$_3$, β—CH$_3$, α—F, β—F, α—OH or =CH$_2$;
$R_{12}$ is H, F, Cl, Br;
$R_{13}$ is H, α—F, α—CH$_3$, β—CH$_3$, α—Cl, β—Cl, β—OH;
$R_{14}$ is H, CH$_3$.

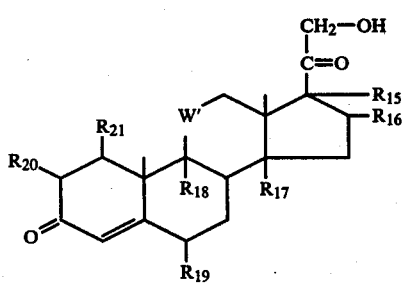

Formula B

In the above Formula B:
W' is

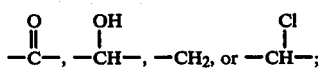

$R_{15}$ is H, α—OH, α—CH$_3$;
$R_{16}$ is H, α—OH, α—CH$_3$;
$R_{17}$ is H, α—OH;
$R_{18}$ is H, α—F, β—F, α—Br, α—Cl, α—OH;
$R_{19}$ is H, β—OH, α—CH$_3$, β—CH$_3$, α—F, α—Cl,
$R_{20}$ is H, α—F, Cl, α—CH$_3$, =CH$_2$;
$R_{21}$ is H, α—OH; with the proviso that one of $R_{20}$ and $R_{21}$ is hydrogen; preferably $R_{17}$, $R_{20}$ and $R_{21}$ are hydrogen.

We claim:

1. A compound of the formula

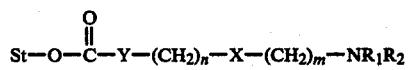

wherein
St is a corticosteroid absent the C-21 hydroxyl of said corticosteroid;
Y is a bound, —O— or —S—;
X is

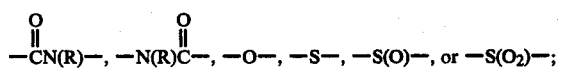

n is an integer of from 2 to 9;
m is an integer of from 1 to 5; with the proviso that the sum of m and n is not greater than 10;
R is H or lower alkyl of from 1 to 4 carbon atoms;
each of R$_1$ and R$_2$ is a lower alkyl group of from 1 to 4 carbon atoms optionally substituted with one hydroxyl group, or R$_1$ and R$_2$ taken together with the nitrogen atom to which each is attached forms a monocyclic heterocyclic ring selected from pyrrolidino, piperidino, morpholino, thiomorpholino, piperazino, or N-(lower)alkyl piperazino; pharmaceutically acceptable addition salts and quaternary ammonium salts thereof with the proviso that when n is 2 or 3 and X is

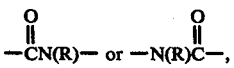

R is lower alkyl.

2. A compound of claim 1 wherein n is 4 to 9.
3. A compound of claim 2 wherein Y is a bond.
4. A compound of claim 2 wherein X is

5. A compound of claim 3 or 4 wherein n is 4 to 6.
6. A compound of claim 5 wherein the corticosteroid forming the St moiety is 6α-methylprednisolone, hydrocortisone, corticosterone, prednisone, prednisolone, triamcinolone, dexamethasone, betamethasone, flumethasone, 11-deoxycorticosterone, fluprednisolone, 9α-fluorohydrocortisone, paramethasone, chlorprednisone or dehydrocorticosterone.
7. A compound of claim 5 which is the N,N,N'-triethylethylenediamine amide of methylprednisolone 21-hemisuberate (HCl salt).
8. A compound of claim 5 which is the
N,N,N'-trimethylethylenediamine amide of methylprednisolone 21-hemisuberate (HCl salt),
N,N-diethylethylene diamine amide of methylprednisolone 21-hemisuberate (HCl salt),
N,N,N'-trimethylethylenediamine amide of methylprednisolone 21-hemisuccinate,
N,N,N'-trimethylethylenediamine amide of methylprednisolone 21-hemiadipate (HCl salt),
N,N,N'-triethylethylenediamine amide of methylprednisolone 21-hemiadipate (HCl salt).
9. A pharmaceutical composition comprising an effective quantity of a compound of claim 1 as a sterile aqueous solution.
10. A composition of claim 9 which is in unit dosage form.
11. A composition of claim 9 or 10 wherein the compound is the
N,N,N'-trimethylethylenediamine amide of methylprednisolone 21-hemisuberate (HCl salt),
N,N-diethylethylene diamine amide of methylprednisolone 21-hemisuberate (HCl salt),
N,N,N'-triethylethylenediamine amide of methylprednisolone 21-hemisuberate (HCl salt),
N,N,N'-trimethylethylenediamine amide of methylprednisolone 21-hemisuccinate,
N,N,N'-trimethylethylenediamine amide of methylprednisolone 21-hemiadipate (HCl salt),
N,N,N'-triethylethylenediamine amide of methylprednisolone 21-hemiadipate (HCl salt).
12. A pharmaceutical composition comprising an effective quantity of a compound of the formula

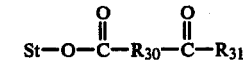

wherein St is a corticosteroid absent the C-21 hydroxyl of said corticosteroid; R$_{30}$ is —(CH$_2$)$_p$—Z$_1$—(CH$_2$)$_p$— or —Z$_2$—(CH$_2$)$_p$— wherein p is an integer of from 1 to 8, Z$_1$ is —O— or —S—, and Z$_2$ is a bound, —O— or —S—; and $R_{31}$ is piperazino or N-(lower)alkylpiperazino; with the proviso that when $Z_2$ is a bond, p is other than the integer 1; pharmaceutically acceptable acid addition salts and quaternary ammonium salts thereof; as a sterile aqueous solution suitable for injection or infusion.

13. An injectable composition of claim 12 which is in unit dosage form.

14. A composition of claim 12 or 13 wherein the corticosteroid forming the St moiety is 6α-methylprednisolone, hydrocortisone, corticosterone, prednisone, prednisolone, triamcinolone, dexamethasone, betamethasone, flumethasone, 11-deoxycorticosterone, fluprednisolone, 9α-fluorohydrocortisone, paramethasone, chlorprednisone or dehydrocorticosterone.

15. A composition of claim 14 wherein the compound is methylprednisolone, 21-[8-(4-methylpiperazino-8-oxo-octanoate], monohydrochloride.

* * * * *